US009388363B2

(12) United States Patent
Goodson et al.

(10) Patent No.: US 9,388,363 B2
(45) Date of Patent: *Jul. 12, 2016

(54) ULTRASONIC AND MEGASONIC METHOD FOR EXTRACTING PALM OIL

(71) Applicant: Megasonic Sweeping, Incorporated, Trenton, NJ (US)

(72) Inventors: J. Michael Goodson, Skillman, NJ (US); Lim Teong Kheng, Pinang (MY)

(73) Assignee: MEGASONIC SWEEPING, INCORPORATED, Trenton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/209,506

(22) Filed: Mar. 13, 2014

(65) Prior Publication Data

US 2014/0275587 A1 Sep. 18, 2014

Related U.S. Application Data

(63) Continuation-in-part of application No. 13/844,097, filed on Mar. 15, 2013, now Pat. No. 8,748,642.

(51) Int. Cl.
*C07C 51/42* (2006.01)
*C11B 1/10* (2006.01)
*C11B 1/04* (2006.01)

(52) U.S. Cl.
CPC .. *C11B 1/106* (2013.01); *C11B 1/04* (2013.01)

(58) Field of Classification Search
CPC ................ B01J 9/10; C11B 1/06; C11B 1/10
IPC ......................................... B01J 9/10554, 9/175
See application file for complete search history.

(56) References Cited

U.S. PATENT DOCUMENTS

| | | | |
|---|---|---|---|
| 2006/0204624 A1 | 9/2006 | Patist et al. | |
| 2008/0312460 A1 | 12/2008 | Goodson | |
| 2010/0015302 A1 | 1/2010 | Bates et al. | |
| 2012/0083618 A1 | 4/2012 | Adnan et al. | |

FOREIGN PATENT DOCUMENTS

| | | | |
|---|---|---|---|
| WO | WO2012/106768 A1 | | 8/2012 |
| WO | WO 2012106766 A1 | * | 8/2012 |
| WO | WO2012/167315 A1 | | 12/2012 |
| WO | WO 2012167315 A1 | * | 12/2012 |

OTHER PUBLICATIONS

PCT/US2014/027731 International Search Report and Written Opinion, mailing date Jul. 21, 2014; 9 pp.

Sulaiman, A. et al., "Study on the Effectiveness of In-Situ High Intensity Ultrasonic (HIU) in Increasing the Rate of Filtration in Palm Oil Industries," pp. 10, Department of Chemical Engineering, University Teknologi Malaysia, Johor, Malaysia.

Abdurahman, N.H., et al., "Ultrasonic Membrane Anaerobic System (UMAS) for Palm Oil Mill Effluent (POME) Treatment," Intech Open Science/Open minds, Ch. 5, 2013 Abdurahman et al., pp. 107-121.

* cited by examiner

*Primary Examiner* — Deborah D Carr
(74) *Attorney, Agent, or Firm* — K&L Gates LLP

(57) ABSTRACT

A process for extracting palm oil includes an ultrasonic horn press and a megasonic clarifier. The ultrasonic horn press uses ultrasonic vibrations to rupture the palm fruit. After pressing and filtering the palm oil from the ultrasonic horn press, the megasonic clarifier applies megasonic vibrations to clarify the palm oil. The ultrasonic horn press and megasonic clarifier significantly reduce the use of water and minimizes pollution as compared to conventional processes.

13 Claims, 6 Drawing Sheets

ULTRASONIC AND MEGASONIC METHOD FOR EXTRACTING PALM OIL

CROSS REFERENCE TO RELATED APPLICATION

This application is a continuation-in-part of U.S. patent application Ser. No. 13/844,097, filed Mar. 15, 2013, entitled "ULTRASONIC AND MEGASONIC METHOD FOR EXTRACTING PALM OIL," which is hereby incorporated by reference in its entirety.

FIELD OF THE INVENTION

This invention relates generally to processing palm oil, and relates more particularly to a method of using ultrasonic and megasonic vibrations to improve the extraction and clarification of palm oil.

BACKGROUND OF THE INVENTION

Conventional processes for extracting palm oil utilize significant quantities of water and energy and result in a substantial amount of Palm Oil Mill Effluent (POME) and waste water. Conventionally, palm fruit bunches are sterilized and cooked as an initial process. The sterilization and cooking of palm oil fruits is carried out using saturated steam of 100° C. at atmospheric pressure generated from a boiler or furnace. The conventional process uses large amount of water to generate the steam to sterilize the fruits. The time needed for cooking is approximately 1 hour. Then the cooked/sterilized fruits are transferred to a stripper or thresher to break apart fruit bunches and break open the skin of the fruit.

There are several problems associated with the conventional sterilization process. One problem is that it is a wet process, so water consumption is high. Energy consumption is also high because steam has to be generated. Another problem is that large amounts of waste water are generated, and the waste water contains solid and liquid materials that cause pollution problems including greenhouse emissions. Another disadvantage is that the process time is high and the later step of stripping or threshing causes noise and vibration.

After sterilization and stripping/threshing, the conventional palm oil process presses the fruit to extract palm oil and then filters the palm oil. The filtered palm oil is then clarified using a tank and mixing in hot water. The clarification tank is kept at a high temperature ranging from 80° C. to 90° C. by a heating coil and continuous injection of steam to maintain the water levels. Generally, the clarification tank will have a palm oil emulsion to water ratio of 1:3 to 1:5. When the emulsion is introduced to the clarifier tank, it is stirred within the tank for the emulsion to be diluted by the hot water and to separate the oil molecules from the water molecules, which thereafter float to the top of the tank where there is a skimmer or an overflow pipe to collect the crude palm oil. The time it takes for the oil to float up and be collected ranges from 3 to 5 hours.

After the skimming or overflow process, the crude palm oil will still have water and suspended solids, which are removed by a centrifugal decanter system. The dried oil is processed through a vacuum drier to remove any moisture up to the specifications as required by the refineries. The water from the emulsion and the suspended solids are mixed with water and are discharged as sludge periodically and may be treated in a three phase decanter process and channeled to holding tanks and subsequently to effluent ponds around the oil mill as Palm Oil Mill Effluent (POME) together with the waste water from the sterilizer section and other sections of the mill.

The conventional clarification process also has several disadvantages. Water and energy consumption is high because of the need to maintain the water temperature for long periods of time and to power the downstream processes used to remove residual water. These are complicated processes that require significant space at the mill and high maintenance as well as causing noise and vibration. The water-based clarification process produces significant amounts of Palm Oil Mill Effluent (POME), which requires big tracts of land for effluent ponds for treatment. Another disadvantage is the significant loss of crude palm oil through the discharge of the POME.

SUMMARY OF THE INVENTION

The present invention is a process for extracting palm oil includes an ultrasonic horn press and/or a megasonic clarifier. The ultrasonic horn press uses ultrasonic vibrations to rupture heated palm fruit without steaming. After pressing and filtering the palm oil from the ultrasonic horn press, the megasonic clarifier applies megasonic vibrations to clarify the palm oil without adding water.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE PREFERRED EMBODIMENTS

The drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1:
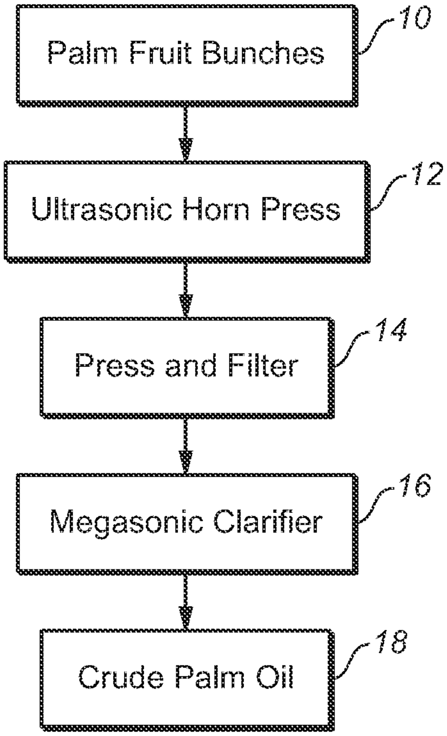
FIG. 1 is a flow chart of an ultrasonic and megasonic method for extracting palm oil according to an embodiment of the present invention.

As shown in FIG. 1, one embodiment of the ultrasonic and megasonic method of the present invention for palm oil extraction starts with gathering palm fruit bunches for processing in step 10. Next, the palm fruit bunches are processed in an ultrasonic horn press 12 to rupture the oil cells in the fruit and heat it at a temperature in the range of 60° C. to 100° C., preferably in the range of 70° C. to 80° C. From there, ruptured fruit is mechanically pressed and filtered in step 14. The palm oil from the pressing step is then clarified in a megasonic clarifier in step 16, which results in clarified crude palm oil in step 18.

Figure 6:
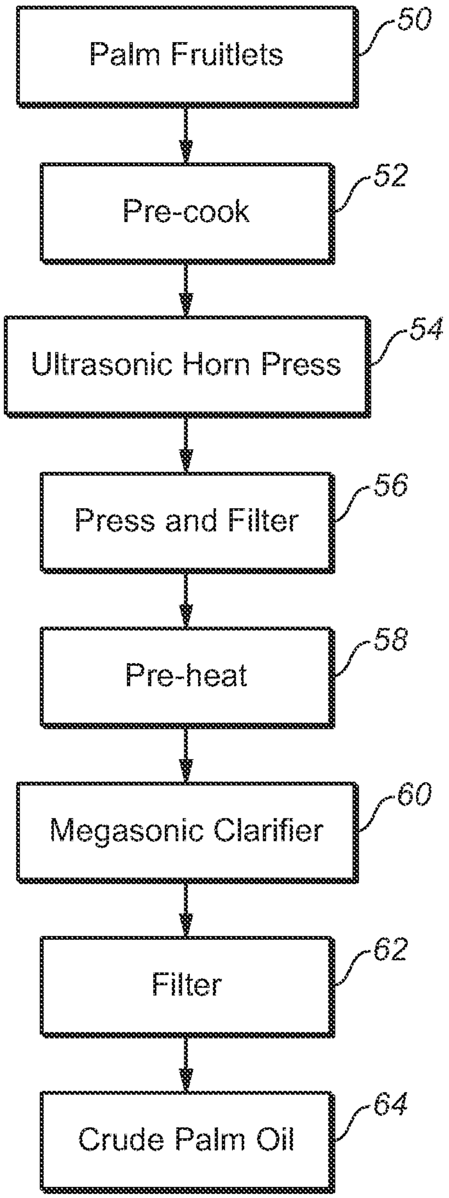
FIG. 6 is a flow chart of an ultrasonic and megasonic method for extracting palm oil according to an embodiment of the present invention.

FIG. 6 illustrates another embodiment of the ultrasonic and megasonic method of the present invention for palm oil extraction. This embodiment starts with palm fruitlets that have been separated from the fruit bunches, as indicated in step 50. Next, the palm fruitlets are pre-cooked in step 52 for about 20 minutes in water at 60° C. to 100° C., preferably in the range of 80° C. to 85° C., to shorten the time in the ultrasonic press and to improve the yield of crude palm oil. After pre-cooking, the palm fruitlets are processed in an ultrasonic horn press 54 to rupture the oil cells in the fruit. Next, the ruptured fruit is mechanically pressed and filtered in step 56, preferably using a screw press. Since the oil that comes out of the ultrasonic horn press of step 54 and the press and filter of step 56 can be thick and highly viscous, it is desirable to heat the oil to 60° C. to 100° C., preferably to about 75° C., prior to megasonic clarification in order to improve the cavitation and streaming activity. The pre-heating is indicated by step 58, and is followed by step 60 of using a megasonic clarifier to clarify the crude palm oil. The clarified crude palm oil from step 60 may need to be filtered in step 62 to remove remaining impurities. The end result is crude palm oil, indicated by step 64.

One aspect of the present invention is replacing a conventional sterilizer with an ultrasonic process using one or more ultrasonic horns to rupture and press the palm fruit. This ultrasonic horn press uses one or more ultrasonic horns to rupture the oil cells within the palm fruit and at the same time to press the oil emulsion out from the fruit. During this process the vibrational energy of the ultrasonic horns is converted to heat, so that the fruit is processed at a preferred temperature of about 70° C. to 80° C., or, alternatively, the fruit is pre-cooked in water at a preferred temperature of about 80° C. to 85° C. before entering the ultrasonic horn press. The combination of vibrational energy and heat energy helps to rupture the oils cells much faster (20 to 30 second) than a conventional process. The amount of heat transferred to the fruits depends on the time of exposure to the ultrasonic horn, or, alternatively, the amount of time and temperature of the pre-cooking step. The ultrasonic horn press alone or in combination with pre-cooking replaces the traditional steam sterilizer.

Figure 2:
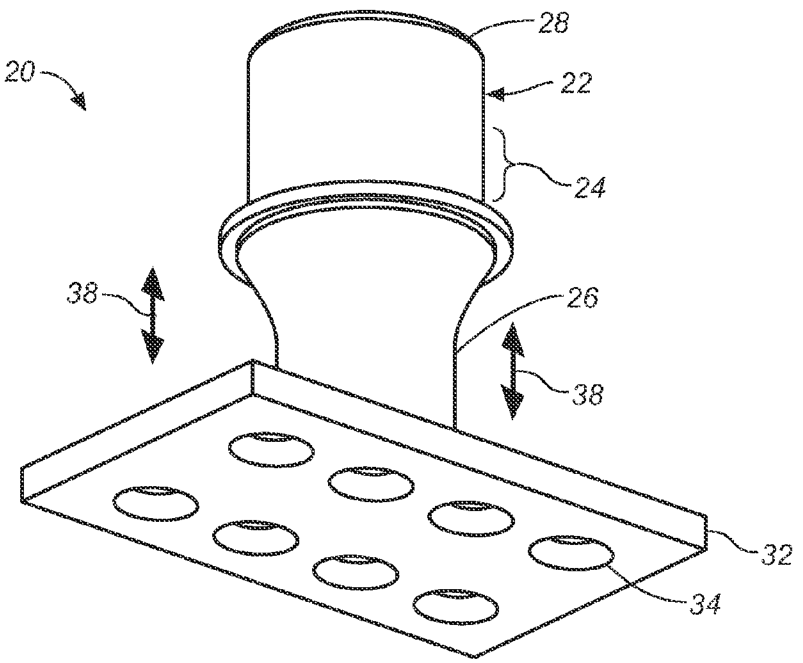
FIG. 2 is a perspective view of an ultrasonic horn press according to an embodiment of the present invention.
Figure 3:
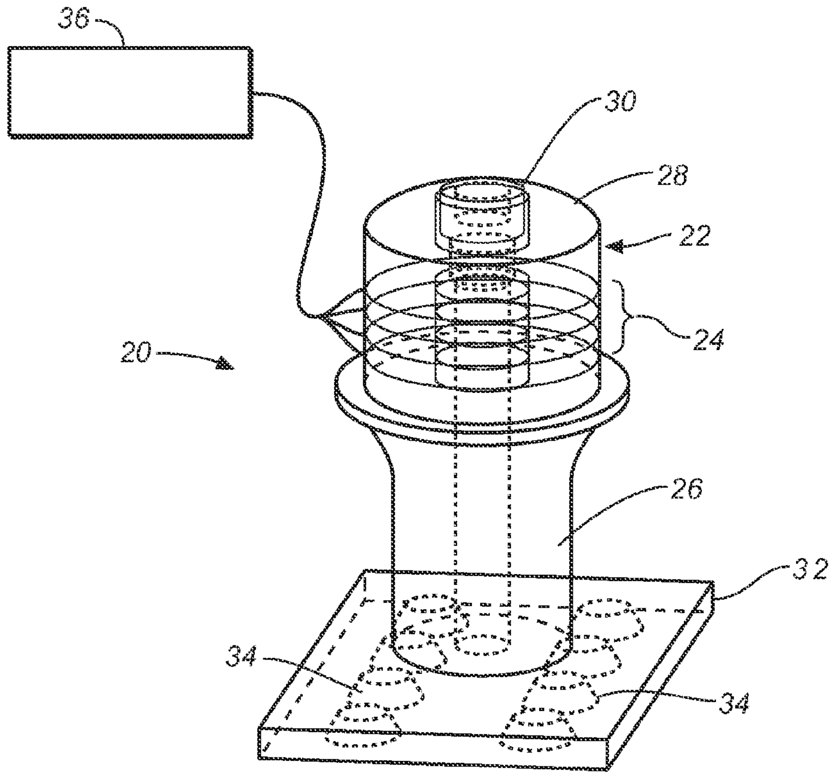
FIG. 3 is a perspective view in phantom of the ultrasonic horn press of FIG. 2 and an associated ultrasonic generator.

One exemplary ultrasonic horn press 20 is shown in FIGS. 2 and 3. The ultrasonic horn press 20 includes an ultrasonic transducer 22 having multiple thickness mode piezoelectric crystals 24 attached to a horn 26. A head mass 28 is located on the side of the piezoelectric crystals 24 opposite the horn 26. The assembly is held together with a bolt 30. The horn 26 includes a plate 32 at the distal end. The plate 32 has several egg-shaped cavities 34 on its bottom surface. The cavities are sized according to the palm fruit and are typically 0.75 inches deep and 1.25 inches long. The piezoelectric crystals 24 are powered by an ultrasonic generator 36 to move the horn 26 and attached plate 32 in an axial direction indicated by arrows 38. The frequency may be, for example, about 20 KHz. A stationary plate (not shown) is located opposite the bottom side of the plate 32. Movement of the plate 32 acts to pulverize the palm fruit between plate 32 and the stationary plate. The above description of the ultrasonic horn press is just exemplary, and other configurations can also be used.

Figure 7:
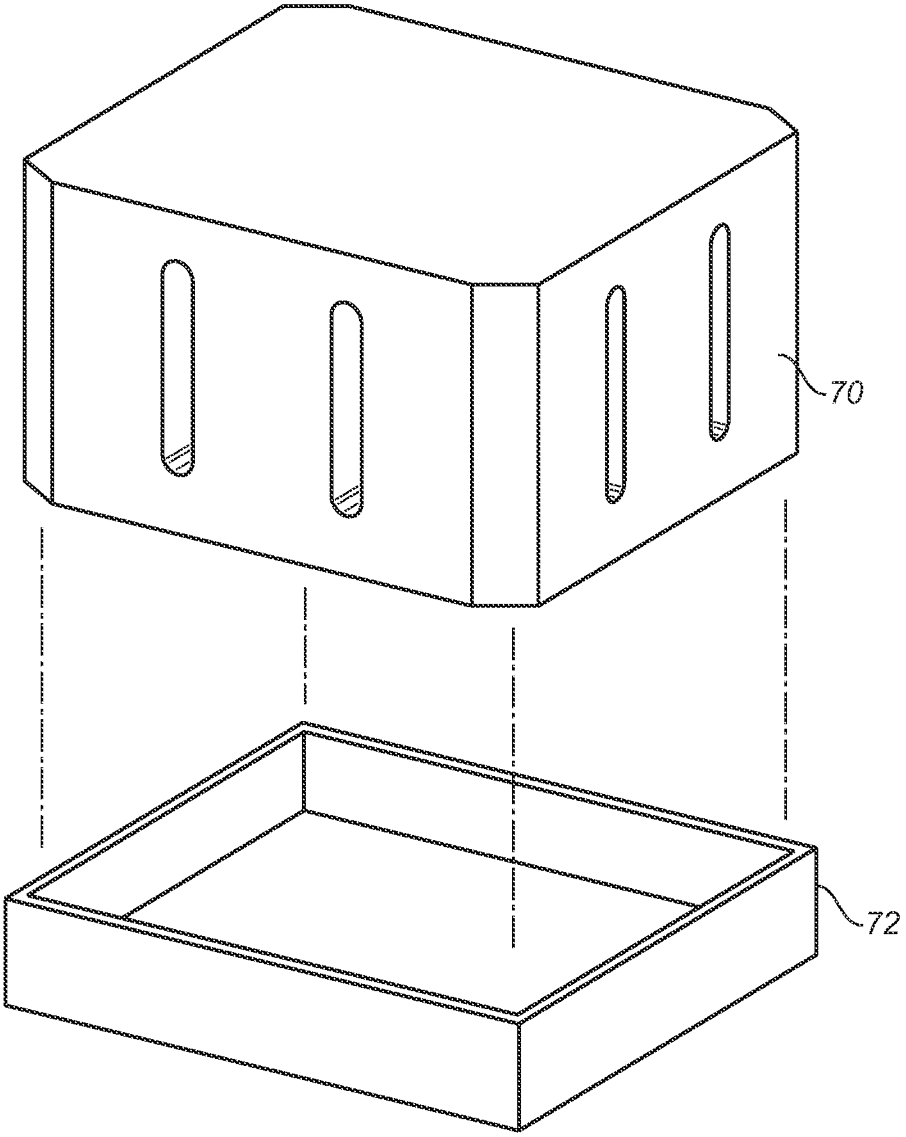
FIG. 7 is a perspective view of an ultrasonic horn press according to an embodiment of the present invention.

FIG. 7 shows another embodiment of an ultrasonic horn 70 for use in the ultrasonic horn press. The ultrasonic horn 70 is preferably mounted in a Standard 3000 ultrasonic welder from Rinco Ultrasonics AG of Romanshorn, Switzerland, which provides ultrasonic vibrations at 20 kHz and is capable of pressing with a force of 3000 N. The preferred size of the bottom surface of the ultrasonic horn 70 that contacts the palm fruit is 190 mm×170 mm. The ultrasonic horn 70 nests in an anvil 72, which is an open container into which the palm fruitlets are placed. The press lowers the ultrasonic horn 70 to compress the palm fruitlets and then excites the horn with 20 kHz ultrasonic vibrations provided by an ultrasonic converter in the Standard 3000 device. The bottom surface of the ultrasonic horn 70, which contacts the top of the palm fruitlets, may be flat or may have egg-shaped cavities like cavities 34 shown in FIGS. 2 and 3.

The ultrasonic horn press has several advantages over conventional palm oil processing methods. It is dry process that does not use steam as does a conventional sterilizer, so water consumption is significantly reduced. The ultrasonic horn press also reduces the amount of energy needed to cook the palm fruits. This process also significantly reduces the process time. The ultrasonic horn press reduces pollution because it reduces the amount of POME that needs to be treated. And this process also promises to yield higher quality oil compared to the conventional process due to low heat transferred to the fruits during ultrasonic horn pressing. Processing the palm fruit in this way at a preferred temperature of about 70° C. to 85° C. yields better quality oil in terms of DOBI value, peroxide value, and Iodine value.

Another aspect of the present invention relates to an improved process for producing clarified crude palm oil from the oil emulsion after the screw press and the filtration system by using a megasonic palm oil clarifier. In the preferred embodiment, the oil emulsion from the press and filtration system, along with any virgin oil extracted by the ultrasonic horn press, is heated to 60° C. to 100° C., preferably in the range of 65° C. to 75° C., to reduce the viscosity of the oil. Through numerous trials, a megasonic frequency of 360 KHz has been determined to produce the best result for separating the oil and the suspended solids within the shortest period of time with the least amount of energy required for the process. The size of the megasonic palm oil clarifier and the supporting systems can be scaled for different palm oil mill sizes and capacities.

Figure 4:
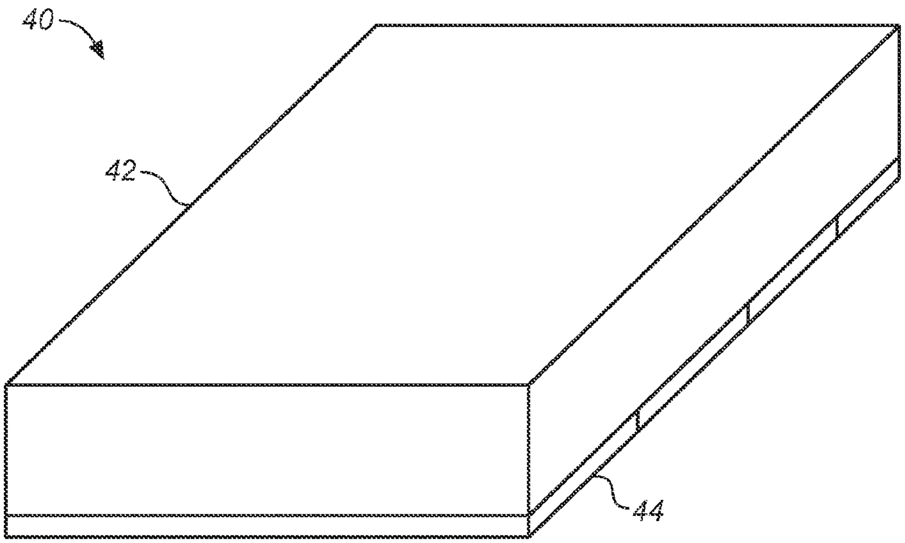
FIG. 4 is a perspective view of a megasonic clarifier according to an embodiment of the present invention.
Figure 5:
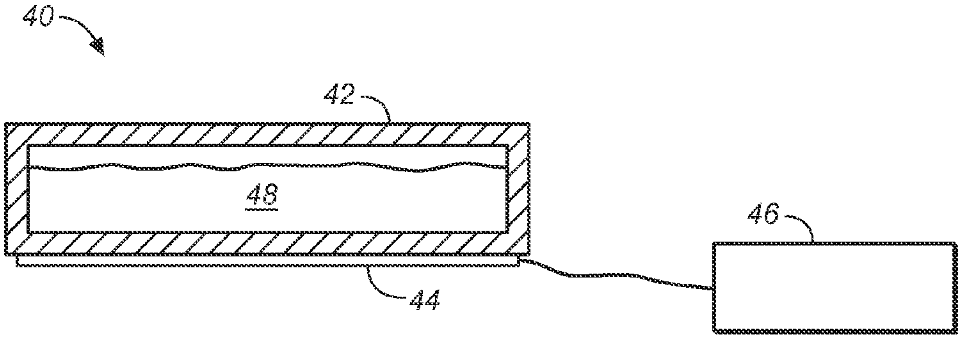
FIG. 5 is a sectional view of the megasonic clarifier of FIG. 4.

In the process for producing clarified crude palm oil after the screw press process, the emulsion is filtered to remove sand, debris and fibers, and the emulsion is placed in the megasonic palm oil clarifier instead of a conventional palm oil clarifier that uses hot water. In one embodiment, shown in FIGS. 4 and 5, the megasonic palm oil clarifier 40 includes a tank 42 with one or more megasonic transducers 44 mounted on the bottom surface. A megasonic generator 46 is connected to the megasonic transducers 44, which supply megasonic vibrations to the palm oil 48 inside the tank.

Figure 8:
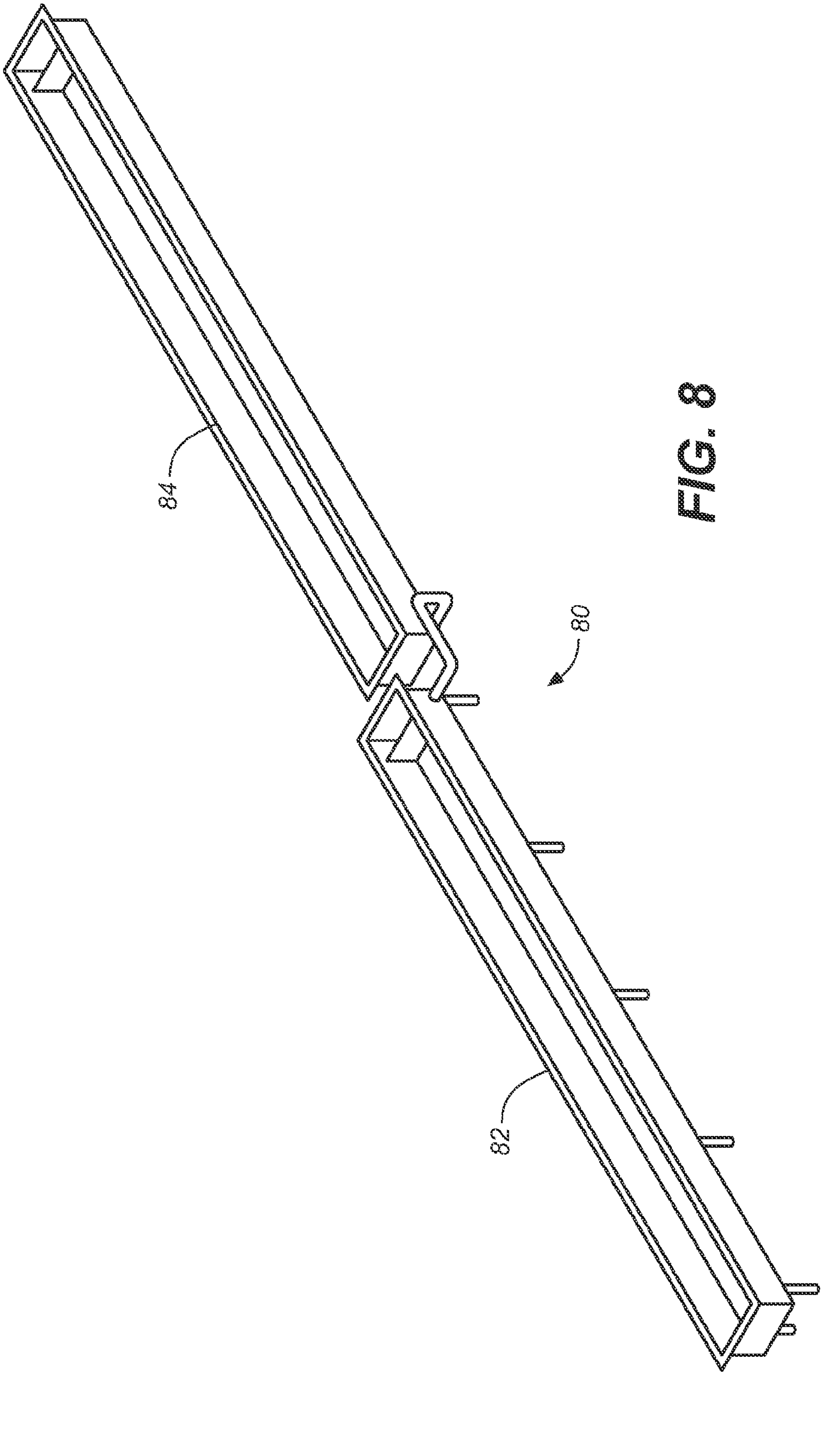
FIG. 8 is a perspective view of a megasonic clarifier according to an embodiment of the present invention.

Another embodiment of the megasonic palm oil clarifier 80 is shown in FIG. 8. This embodiment uses two open tanks 82 and 84 with megasonic transducers mounted on the bottom surfaces of both tanks Crude palm oil to be clarified is piped into tank 82, where it is subjected to megasonic vibrations to clarify the oil. Most of the sludge settles out in tank 82. The clarified palm oil from tank 82 is piped into tank 84, where is it further clarified by megasonic vibrations, resulting in high purity crude palm oil. The megasonic transducers preferably operate at about 360 kHz.

Megasonic waves at the required high frequency generate millions of microscopic bubbles and acoustic streaming in the palm oil emulsion, which helps to separate and extract the oil bearing molecules from the other entrained impurities much faster than the conventional process. The separation of the oil and other impurities takes place immediately upon the application of the megasonic vibrations. The whole process to create a sufficiently clear crude palm oil can take between 10 and 15 minutes, depending on the megasonic frequency, the power applied and the temperature of the palm oil emulsion.

Although experiments showed that 360 KHz is an optimum frequency for the megasonic clarifier, other megasonic frequencies in the range of 300 KHz to 1000 KHz (1 MHz) are also feasible for use with the invention. Testing also showed that the temperature range of 200° F. (93° C.) to 240° F. (116° C.) is particularly advantageous for operation of the megasonic clarifier. In addition, the megasonic transducer or transducers used in the megasonic clarifier can be enclosed and cooled with nitrogen gas.

There are several advantages of the megasonic palm oil clarifier. It provides a simple and reliable process for the oil clarifying stage in the palm oil mill and eliminates the need to add hot water in order to clarify the oil. This process eliminates the need for the centrifugal decanter system to remove debris or impurities from the clarified oil. This process generates much less sludge or waste water as Palm Oil Mill Effluent to be discharged into effluent ponds. This process reduces energy that is used by conventional hot water clarifiers and decanters. This process will generate the optimum oil recovery for the palm oil mill. With this process, water and suspended solids will be collected from the megasonic clarifier and the suspended solids will be filtered and the water collected for further processing and thereafter filtered for recycling purpose.

From the above description, it will be apparent that the invention disclosed herein provides novel and advantageous processes for extracting palm oil. The foregoing discussion discloses and describes merely exemplary methods and embodiments of the present invention. As will be understood by those familiar with the art, the invention may be embodied in various other forms without departing from the spirit or essential characteristics thereof. Accordingly, the disclosure of the present invention is intended to be illustrative, but not limiting, of the scope of the invention, which is set forth in the following claims.

The invention claimed is:

1. A process for extracting palm oil, comprising:
- simultaneously vibrating with an ultrasonic horn and pressing palm fruit to extract palm oil therefrom;
- filtering the extracted palm oil; and
- clarifying the filtered palm oil with megasonic vibrations.

2. A process for extracting palm oil as recited in claim 1, further comprising a step of heating the palm fruit prior to the step of simultaneously vibrating and pressing the same.

3. A process for extracting palm oil as recited in claim 2, wherein the step of heating the palm fruit includes heating the palm fruit in water at a temperature in the range of 60° C. to 100° C.

4. A process for extracting palm oil as recited in claim 2, wherein the step of heating the palm fruit includes heating the palm fruit in water at a temperature in the range of 70° C. to 85° C.

5. A process for extracting palm oil as recited in claim 1, further comprising a step of heating the filtered palm oil prior to the step of clarifying the same.

6. A process for extracting palm oil as recited in claim 5, wherein the step of heating the filtered palm oil includes heating the filtered palm oil to a temperature in the range of 60° C. to 100° C.

7. A process for extracting palm oil as recited in claim 5, wherein the step of heating the filtered palm oil includes heating the filtered palm oil to a temperature in the range of 65° C. to 75° C.

8. A process for extracting palm oil as recited in claim 1, wherein the step of clarifying the filtered palm oil includes supplying unclarified palm oil to a first tank and using megasonic transducers to apply megasonic vibrations to partially clarify the palm oil in the first tank, and then supplying the partially clarified palm oil to a second tank and using megasonic transducers to apply megasonic vibrations to further clarify the palm oil in the second tank.

9. A process for extracting palm oil as recited in claim 1, further comprising a step of filtering the clarified palm oil.

10. A process for extracting palm oil, comprising:
- heating palm fruit in water at a temperature in the range of 70° C. to 85° C.;
- simultaneously vibrating with an ultrasonic horn and pressing the heated palm fruit to extract palm oil;
- filtering the extracted palm oil;
- heating the filtered palm oil to a temperature in the range of 65° C. to 75° C.; and
- supplying the heated and filtered palm oil to a first tank and using megasonic transducers to apply megasonic vibrations to partially clarify the palm oil in the first tank, and then supplying the partially clarified palm oil to a second tank and using megasonic transducers to apply megasonic vibrations to further clarify the palm oil in the second tank.

11. A process for extracting palm oil, comprising:
- heating palm fruit in water at a temperature in the range of 70° C. to 85° C.;
- simultaneously vibrating with an ultrasonic horn and pressing the heated palm fruit to extract palm oil.

12. A process for clarifying palm oil, comprising:
- heating palm oil to a temperature in the range of 65° C. to 75° C.;
- supplying the heated palm oil to a first tank and using megasonic transducers to apply megasonic vibrations to partially clarify the palm oil in the first tank, and then supplying the partially clarified palm oil to a second tank and using megasonic transducers to apply megasonic vibrations to further clarify the palm oil in the second tank.

13. The process for extracting palm oil recited in claim 1, wherein the palm fruit being pressed are dry palm fruit.

* * * * *